US012678026B2

(12) United States Patent
Lee et al.

(10) Patent No.: US 12,678,026 B2
(45) Date of Patent: Jul. 14, 2026

(54) IMAGE PROCESSING METHOD AND IMAGE PROCESSING APPARATUS

(71) Applicant: MEDIT CORP., Seoul (KR)

(72) Inventors: Dong Hoon Lee, Seoul (KR); Sung Bin Im, Seoul (KR)

(73) Assignee: MEDIT CORP., Seoul (KR)

( * ) Notice: Subject to any disclaimer, the term of this patent is extended or adjusted under 35 U.S.C. 154(b) by 309 days.

(21) Appl. No.: 18/274,799

(22) PCT Filed: Jan. 28, 2022

(86) PCT No.: PCT/KR2022/001616
§ 371 (c)(1),
(2) Date: Jul. 28, 2023

(87) PCT Pub. No.: WO2022/164267
PCT Pub. Date: Aug. 4, 2022

(65) Prior Publication Data
US 2024/0306885 A1 Sep. 19, 2024

(30) Foreign Application Priority Data

Feb. 1, 2021 (KR) ........................ 10-2021-0014239

(51) Int. Cl.
*A61B 1/00* (2006.01)
*A61B 1/24* (2006.01)
(Continued)

(52) U.S. Cl.
CPC ...... *A61B 1/00062* (2013.01); *A61B 1/00055* (2013.01); *A61B 1/00059* (2013.01);
(Continued)

(58) Field of Classification Search
CPC ............ A61B 1/00062; A61B 1/00055; A61B 1/00059; A61B 1/24; A61B 5/0062;
(Continued)

(56) References Cited

U.S. PATENT DOCUMENTS

| | | | | |
|---|---|---|---|---|
| 11,478,132 B2 * | 10/2022 | Kopelman | ........... | A61B 5/0088 |
| 2007/0167686 A1 * | 7/2007 | McGrath | ............ | A61B 1/00087 |
| | | | | 600/188 |

(Continued)

FOREIGN PATENT DOCUMENTS

| | | |
|---|---|---|
| EP | 3 597 146 A1 | 1/2020 |
| JP | 2018-149187 A | 9/2018 |

(Continued)

OTHER PUBLICATIONS

International Search Report for PCT/KR2022/001616 dated May 10, 2022.

(Continued)

*Primary Examiner* — Howard D Brown, Jr.
(74) *Attorney, Agent, or Firm* — Sughrue Mion, PLLC

(57) ABSTRACT

An image processing apparatus and an image processing method, according to the present invention, may sense an identifier positioned in a tip to identify unique information such as a serial number of the tip, and may update tip use information assigned to the identified unique information. In some cases, in connection with updating the tip use information, the use information may also be selectively updated based on the type of a scan target to be scanned. Alternatively, a scanning operation of the image processing apparatus may be restricted when a predetermined elapsed time from the removal to the mounting of the tip after scanning an oral cavity is not ensured. Due to the above-mentioned configuration, a user can conveniently recognize when to replace the tip.

14 Claims, 23 Drawing Sheets

(51) Int. Cl.
    *A61B 5/00*       (2006.01)
    *A61B 90/00*     (2016.01)
    *A61C 9/00*       (2006.01)

(52) U.S. Cl.
    CPC .............. *A61B 1/24* (2013.01); *A61B 5/0062*
        (2013.01); *A61B 5/0088* (2013.01); *A61B*
        *90/08* (2016.02); *A61C 9/006* (2013.01); *A61B*
        *2090/0805* (2016.02); *A61B 2090/0806*
        (2016.02)

(58) Field of Classification Search
    CPC .................. A61B 5/0088; A61B 90/08; A61B
        2090/0805; A61B 2090/0806; A61B 1/00;
        A61B 5/00; A61B 90/00; A61B
        2090/0803; A61C 9/006; A61C 9/00;
        A61C 9/0053; A61C 19/04
    See application file for complete search history.

(56)            References Cited

U.S. PATENT DOCUMENTS

| | | | |
|---|---|---|---|
| 2019/0201104 A1* | 7/2019 | Shelton, IV | ......... A61B 1/0005 |
| 2020/0288959 A1 | 9/2020 | Lahti et al. | |
| 2025/0194907 A1* | 6/2025 | Kopelman | ............. G16H 40/67 |

FOREIGN PATENT DOCUMENTS

| | | | |
|---|---|---|---|
| KR | 10-2007-0028984 A | 3/2007 |
| KR | 10-2012-0133246 A | 12/2012 |
| KR | 10-2016-0041632 A | 4/2016 |
| KR | 10-2152921 B1 | 9/2020 |
| WO | 2020/173955 A1 | 9/2020 |

OTHER PUBLICATIONS

Korean Office Action dated Jun. 3, 2022 in Korean Application No. 10-2021-0014239.
Korean Final Office Action dated Feb. 21, 2023 in Korean Application No. 10-2021-0014239.

* cited by examiner

Figure 13:
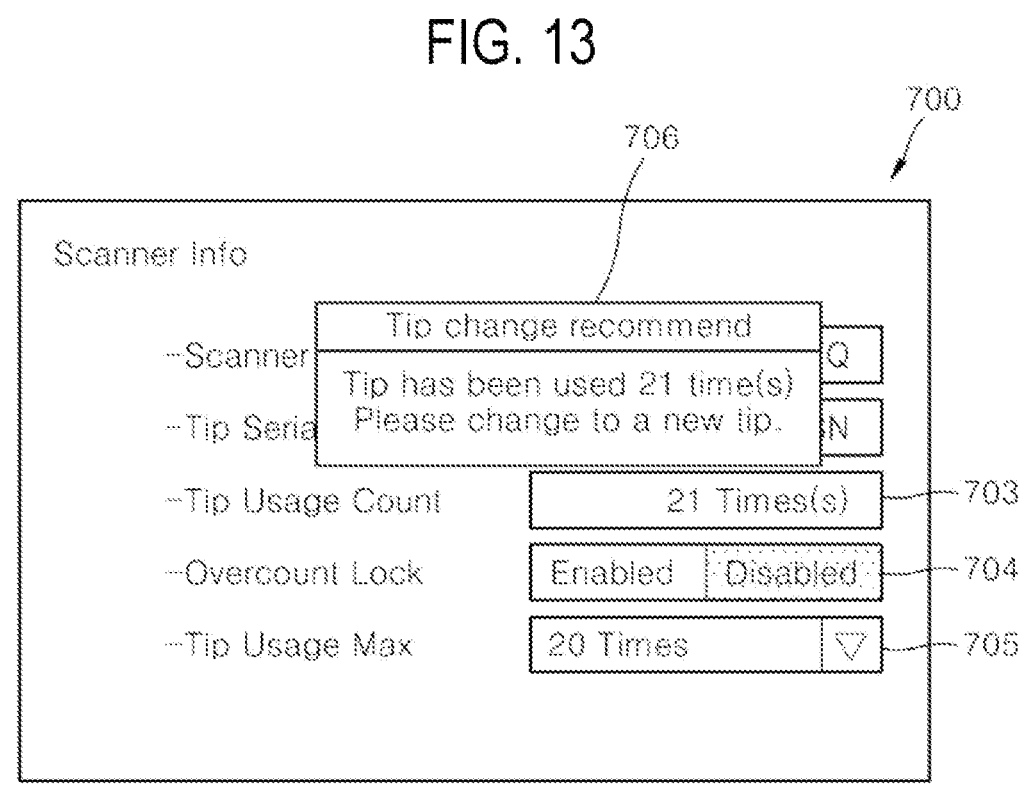

Scanner Info

-Scanner ... Q

-Tip Seria ... N

Tip change recommend

Tip has been used 21 time(s)
Please change to a new tip.

-Tip Usage Count          21 Times(s)          ~703

-Overcount Lock          Enabled  Disabled          ~704

-Tip Usage Max          20 Times          ▽          ~705

FIG. 15

Start

Identifying unique information — S210

Detecting target — S220

Updating data — S230

End

FIG. 17

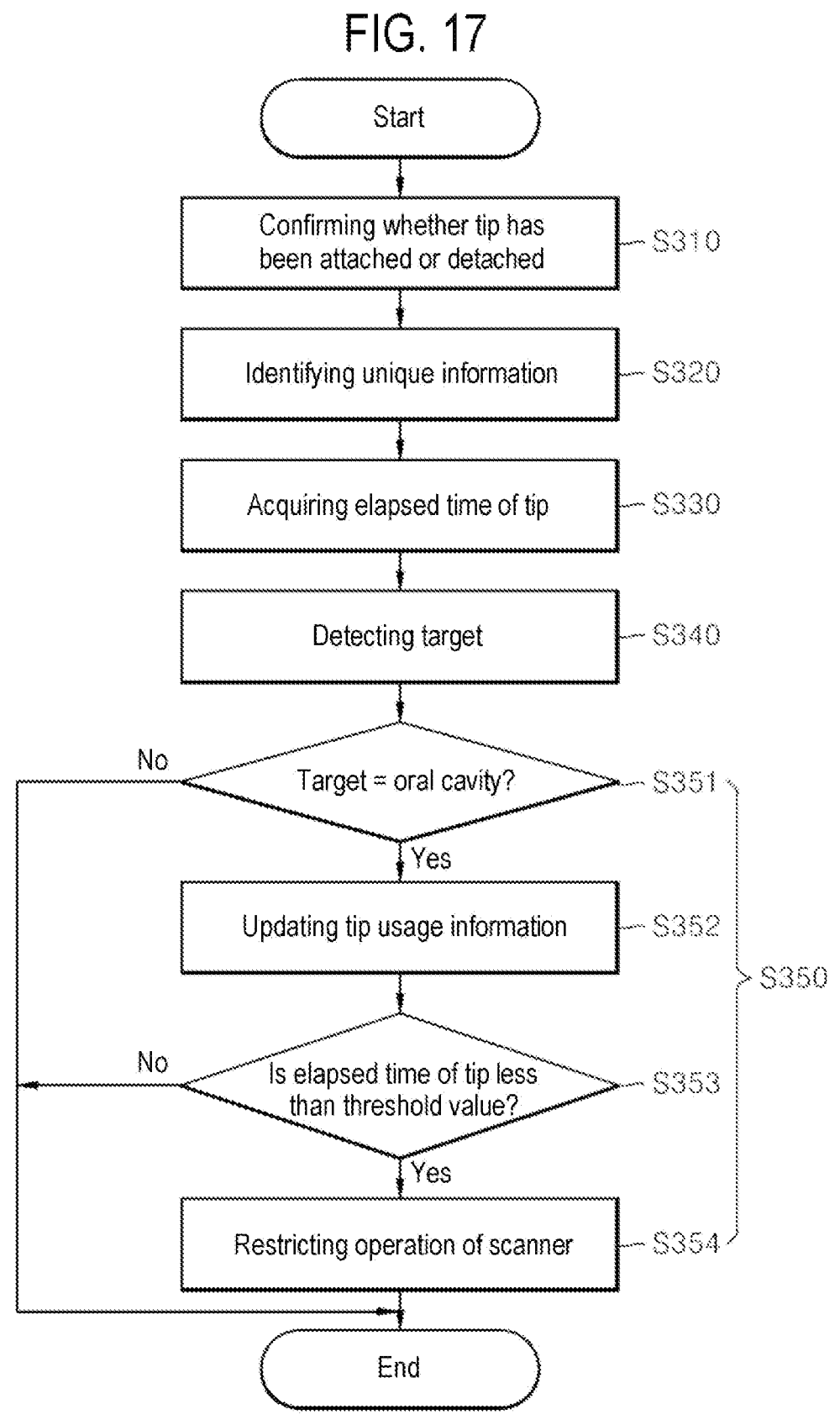

Start

Confirming whether tip has been attached or detached — S310

Identifying unique information — S320

Acquiring elapsed time of tip — S330

Detecting target — S340

Target = oral cavity? — S351

No

Yes

Updating tip usage information — S352

S350

Is elapsed time of tip less than threshold value? — S353

No

Yes

Restricting operation of scanner — S354

End

IMAGE PROCESSING METHOD AND IMAGE PROCESSING APPARATUS

CROSS REFERENCE TO RELATED APPLICATIONS

This application is a National Stage of International Application No. PCT/KR2022/001616 filed Jan. 28, 2022, claiming priority based on Korean Patent Application No. 10-2021-0014239 filed Feb. 1, 2021.

TECHNICAL FIELD

The present disclosure relates to an image processing apparatus and an image processing method.

BACKGROUND

Conventional methods, which have been used to acquire information about a patient's oral cavity, include a method for acquiring images of the oral cavity surface through a camera from multiple angles, or a method for acquiring information about the inside of the oral cavity through an X-ray or CT scan. However, these methods have been problematic in that the methods had to be performed separately during medical treatment by a practitioner, and thus caused inconvenience to the patient.

In order to solve such problems, methods that can easily and quickly acquire information about the surface of a patient's oral cavity by using a three-dimensional scanner have been developed and used. In particular, a method for acquiring information about a patient's teeth, gingiva, and dental arch by inserting and withdrawing a three-dimensional intraoral scanner directly into and from the patient's oral cavity has been used.

In the case of a three-dimensional intraoral scanner, a tip formed at one end of the intraoral scanner is inserted into a patient's oral cavity during a scanning process. Accordingly, during the scanning process, droplets from the inner wall of the oral cavity, teeth, or gingiva, and intraoral tissue may adhere to the surface of the tip, thereby contaminating the tip.

The contaminated tip needs to be separated from the body of the intraoral scanner and cleaned. When the intraoral scanner is used more than a predetermined number of times, hygiene problems due to wear of the tip, etc. may occur in the process of scanning the inside of a patient's oral cavity. Accordingly, it is necessary to replace the tip after using the tip more than the predetermined number of times. In the past, a user managed a tip by manually noting the number of times the tip was used, which was inefficient and inaccurate in terms of management.

SUMMARY

To solve the problems in the background art as described above, an image processing apparatus according to the present disclosure updates usage information of a tip through an attachment/detachment confirmation means.

Further, an image processing apparatus according to the present disclosure updates the usage information of the tip by using an identifier located inside the tip.

Further, an image processing method according to the present disclosure updates usage information of a tip via at least one of the attachment/detachment confirmation means or an identifier located inside the tip.

Technical objectives to be achieved by the present disclosure are not limited to the above-described technical objectives, and other technical objectives not described will be clearly understood by a person skilled in the art from the description below.

In order to achieve the above-described objectives, an image processing apparatus is proposed which is capable of selectively updating usage information of a tip by means of an attachment/detachment confirmation means formed on an attachment/detachment surface at one end of a scanner body which is coupled to the tip.

Further, an image processing apparatus is proposed in which an identifier is disposed on a tip that is detachably coupled to a scanner body, and in which usage information of the tip can be selectively updated through a process of detecting the identifier.

Further, the image processing apparatus may use an image processing method for automatically updating usage information of a tip.

The image processing apparatus and image processing method according to the present disclosure may be used to make it possible for a user to check automatically updated usage information of a tip. Therefore, the image processing apparatus and image processing method according to the present disclosure may provide a hygienic treatment environment to a patient.

Further, through the attachment/detachment confirmation means formed on the scanner body, it is possible to easily detect whether the tip is attached to the scanner body, and to quickly update usage information of the tip.

Further, the identifier is not converted into a three-dimensional model, and thus a reliable three-dimensional model may be acquired.

Further, through the attachment/detachment confirmation means formed on the attachment/detachment surface constituting the scanner body, the usage information of the tip may be confirmed doubly with the identifier.

Further, usage information may be selectively updated depending on the type of scan target, thereby preventing unnecessary updating of the usage information.

Further, the attachment/detachment confirmation means may be used to confirm an elapsed time from when the tip is detached to when the tip is reattached, and to selectively limit a scanning operation based on the elapsed time, thereby providing a hygienic treatment environment to a patient.

BRIEF DESCRIPTION OF DRAWINGS

FIGS. 2A and 2B are a perspective view and a cross-sectional view of a tip in an image processing apparatus according to the present disclosure.

FIG. 4 illustrates a cross-sectional view of a tip and a scanner body coupled to each other in an image processing apparatus according to the first embodiment of the present disclosure.

FIGS. 5A, 5B, and 5C illustrate a perspective view and cross-sectional views of a tip in an image processing apparatus according to a second embodiment of the present disclosure.

FIG. 8 is a view illustrating a time point of performing a scanning process in an image processing apparatus according to a third embodiment of the present disclosure.

FIG. 10 illustrates a cross-sectional view of a tip and a scanner body coupled to each other in an image processing apparatus according to a fifth embodiment of the present disclosure.

FIGS. 12 and 13 illustrate a process of updating usage information of a tip in an image processing apparatus according to the present disclosure.

FIG. 15 is a flowchart of an image processing method according to a second embodiment of the present disclosure.

FIG. 17 is a flowchart of an image processing method according to a third embodiment of the present disclosure.

Figure 1:
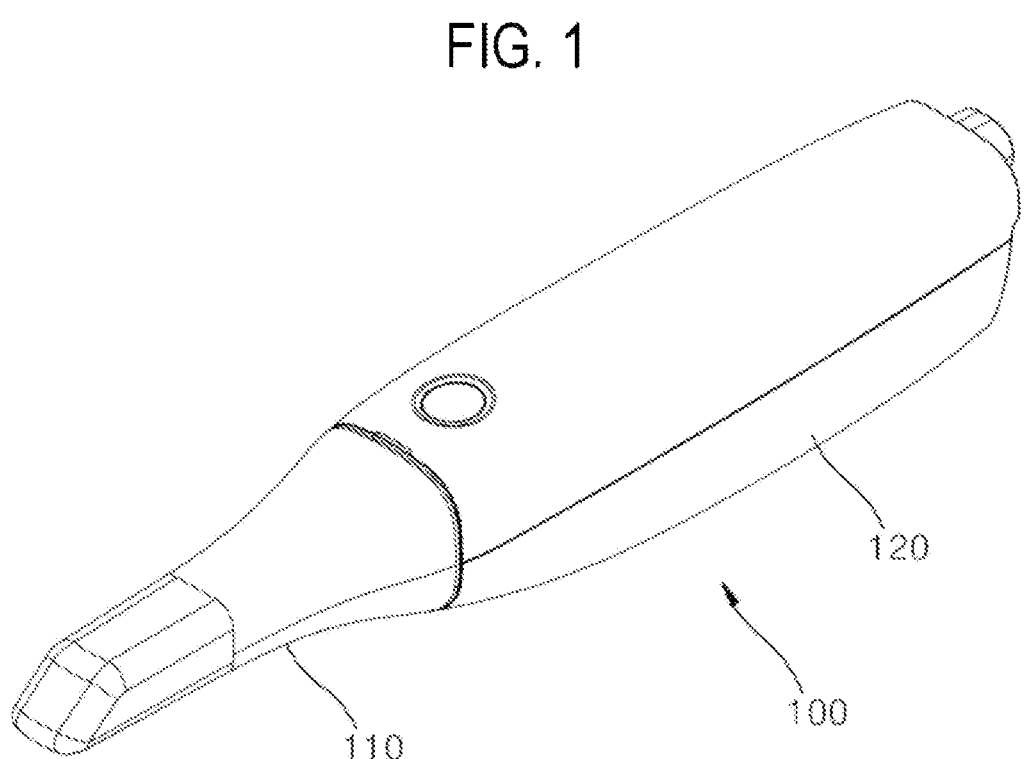
FIG. 1 is a perspective view of a scanner including elements of an image processing apparatus according to the present disclosure.

reference numerals to elements in each drawing, the same elements will be designated by the same reference numerals if possible, although they are shown in different drawings. Further, in the following description of embodiments of the present disclosure, a detailed description of known functions and configurations incorporated herein will be omitted when it is determined that the description interferes with the understanding of the embodiments of the present disclosure.

Terms, such as first, second, A, B, (a), (b) or the like may be used herein when describing elements of the embodiments of the present disclosure. These terms are used merely to distinguish one element from other elements, and a property, an order, a sequence, and the like of a corresponding element are not limited by the terms. Further, unless otherwise defined, all terms used herein, including technical or scientific terms, have the same meanings as those generally understood by a person skilled in the art to which the present disclosure pertains. Such terms as those defined in a generally used dictionary should be interpreted to have meanings matching the contextual meanings in the relevant field of art, and are not to be interpreted to have ideal or excessively formal meanings unless clearly defined in the present disclosure.

FIG. 1 is a perspective view of a scanner 100 including elements of an image processing apparatus according to the present disclosure.

Referring to FIG. 1, an image processing apparatus according to the present disclosure includes a tip 110 and a scanner body 120. The scanner body 120 may include at least one camera therein, and may acquire data from the camera. In this case, the data acquired by the scanner body 120 may be image data obtained by scanning a scan target. The tip 110 is a portion that is inserted into or withdrawn from a patient's oral cavity. The tip 110 may be coupled to

[Description of symbols]

| | |
|---|---|
| 110: Tip | 111: First opening |
| 112: Second opening | 113: Optical member |
| 114: Identifier | 115: Inner surface |
| 116: Receiving groove | 120: Scanner body |
| 121: Housing | 122, 122a, 122b: Camera |
| 123: Light projector | 124: Attachment/detachment surface |
| 125: Attachment/detachment confirmation means | 200: Controller |
| 210: Identifier detector | 220: Data updater |
| 230: Target detector | 240: Checker |
| 300: Display | 500: Input area |
| 510: First area | 520: Second area |
| 700: User interface | 701: Scanner information |
| 702: Tip information | 703: Tip usage information |
| 704: Excessive scanning limit | 705: Maximum tip usage count |
| 706: Notification message | |
| S110: Unique information identification step | S111: Identifier detection step |
| S112: Unique information extraction step | S120: Data updating step |
| S210: Unique information identification step | S220: Target detection step |
| S230: Data updating step | S231: Scan target determination step |
| S232: Usage information updating step | |
| S310: Attachment/detachment confirmation step identification step | S320: Unique information |
| S330: Elapsed time acquisition step | S340: Target detection step |
| S350: Operation control step | S351: Target determination step |
| S352: Elapsed time determination step | S353: Operation restriction step |
| S410: Attachment/detachment confirmation step | S420: Elapsed time acquisition step |
| S430: Target detection step | S440: Target determination step |
| S450: Usage information updating step | S460: Elapsed time determination step |
| S470: Operation restriction step | |

DETAILED DESCRIPTION

Hereinafter, some embodiments will be described in detail with reference to the accompanying drawings. In adding and integrally formed with one end of the scanner body 120. The tip 110 and the scanner body 120 are coupled to each other to form a single scanner 100. The scanner 100 may be a three-dimensional scanner.

Hereinafter, a configuration of the tip 110 will be described in detail.

Through the tip 110, data indicating a scan target to be scanned may be easily received in the scanner body 120. More specifically, the tip 110 functions as a passage for guiding light reflected from a surface of the scan target to be easily received in the scanner body 120. The scan target is a target of which scan information is desired to be acquired. For example, the scan target may be the patient's actual oral cavity, including teeth and gingiva. Further, the scan target may be a plaster cast obtained by taking an impression of the patient's oral cavity with alginate or the like. The image processing apparatus according to the present disclosure may selectively update tip usage information according to the scan target, which will be described later.

The tip 110 may be formed of a variety of materials. The tip 110 may be inserted into and withdrawn from the patient's oral cavity, and may come into contact with the patient's teeth, gingiva, inner wall of cheeks, tongue, palate, and the like. Accordingly, the tip 110 may be formed of a material that is harmless to the human body and lightweight, and the tip 110 may be formed of, for example, a plastic material. However, this is merely an example, and the material of the tip 110 is not limited to plastic. The tip 110 may be formed of any material that is harmless to the human body and lightweight, and the tip 110 may be formed of a composite material if necessary.

Figure 2A:
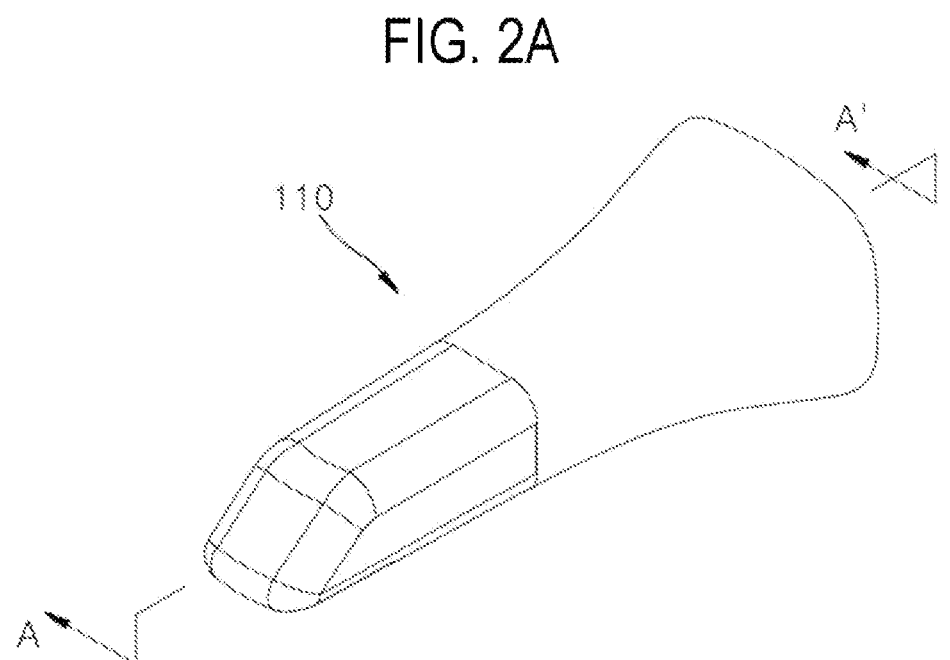
Figure 2B:
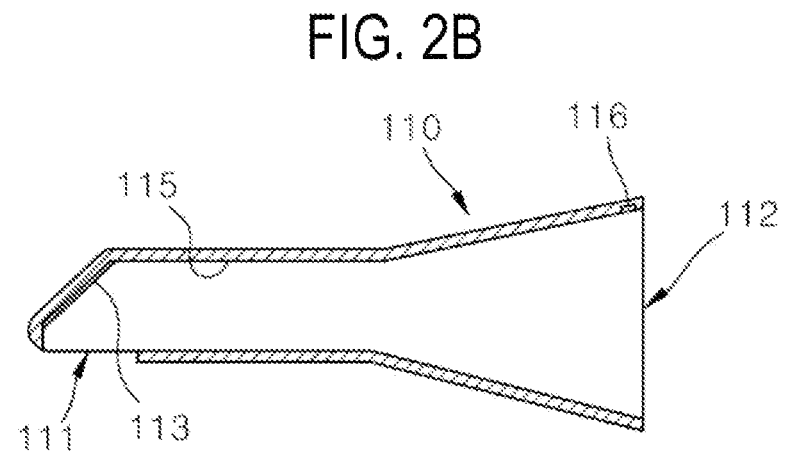

FIGS. 2A and 2B are is a perspective view and a cross-sectional view of a tip in an image processing apparatus according to the present disclosure. More specifically, FIG. 2A is a perspective view of the tip 110, and FIG. 2B is a cross-sectional view taken along line A-A' in FIG. 2A.

The tip 110 will be described in detail with reference to FIG. 2. The tip 110 includes a first opening 111 and a second opening 112. The first opening 111 is formed at one end of the tip 110. The first opening 111 may be formed in a direction toward a scan target, and a user can easily perform a scanning process. For example, the first opening 111 may be formed to have a constant angle with respect to the longitudinal direction of the tip 110. At this time, the longitudinal direction of the tip 110 may refer to a direction in which the tip 110 and the scanner body 120 are coupled to each other.

Further, the second opening 112 is formed at the other end of the tip 110. By forming the second opening 112 at the other end of the tip 110, the first opening 111 and the second opening 112 may communicate with the inside of the tip 110, and an inner surface 115 may be formed by the communication of the first opening 111 and the second opening 112. Accordingly, light may pass through the inside of the tip 110 formed in a communicating structure. More specifically, light generated inside the scanner body 120 may be irradiated from the second opening 112 toward the first opening 111, or light reflected from the surface of the scan target may be introduced toward the second opening 112 through the first opening 111 and received in the scanner body 120.

Further, the tip 110 may include an optical member 113. The optical member 113 may be disposed on the inner surface 115 of the tip 110. The optical member 113 changes the path of light by refracting or reflecting light incident on the inside of the tip 110. For example, light incident on the optical member 113 through the first opening 111 may be reflected to have a reflection angle equal to the angle of incidence with respect to the normal of the optical member 113. The light incident on the optical member 113 may be light reflected from the surface of the scan target and introduced into the tip. The light having the path changed by the optical member 113 may be received by the scanner body 120 formed at the second opening 112 side.

The optical member 113 may be, but is not limited to, a mirror or a lens for performing the function as described above, and may be any means capable of changing the path of light, such as refracting or reflecting incident light. For example, the optical member 113 may be a type of electronic device capable of changing the path of light. The optical member 113 may be disposed at a suitable location for changing the path of light, incident from the first opening 111, towards the second opening 112.

The tip 110 may include a receiving groove 116 at the second opening 112 side. The receiving groove 116 may receive an attachment/detachment confirmation means (not shown) of the scanner body 120, which will be described later. The receiving groove 116 may be recessed in a shape corresponding to the shape of the attachment/detachment confirmation means to receive the attachment/detachment confirmation means, but is not necessarily limited thereto, and may not be recessed, unlike what is shown in the drawings.

Hereinafter, the scanner body 120 will be described in detail.

Figure 3:
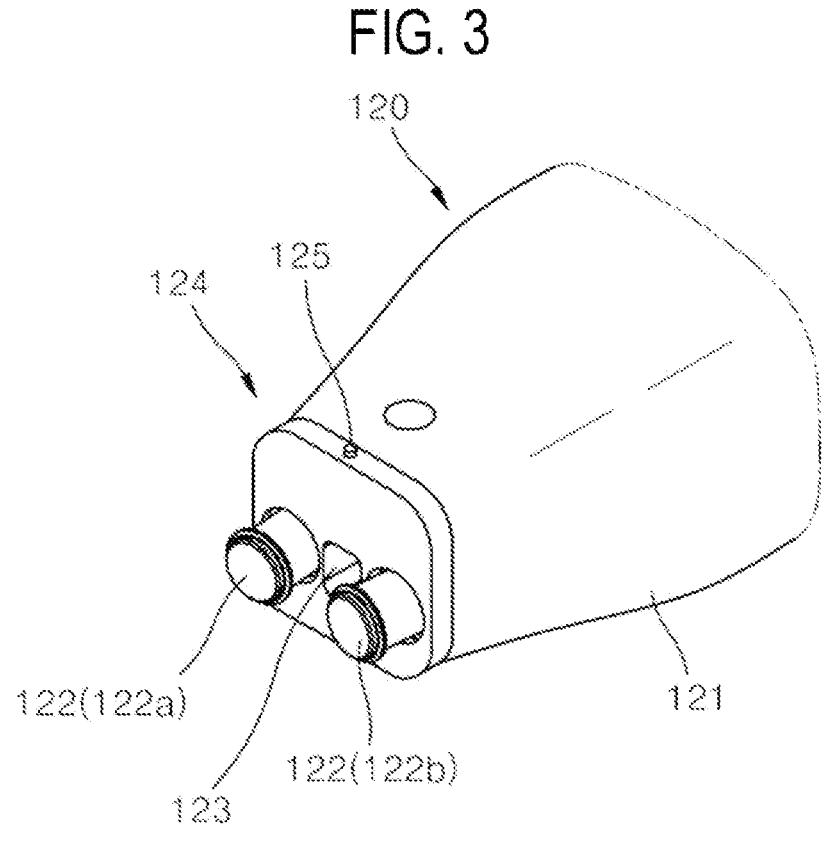
FIG. 3 illustrates a perspective view of a portion of a scanner in an image processing apparatus according to a first embodiment of the present disclosure.

FIG. 3 illustrates a perspective view of a portion of a scanner body in an image processing apparatus according to a first embodiment of the present disclosure.

Referring to FIG. 3, in the image processing apparatus according to the present disclosure, the scanner body 120 may include a housing 121 that encloses components inside the scanner body 120. The housing 121 forms an outer surface that enables a user to grip the scanner 100, and safely protects the components disposed inside the housing 121 from an external environment. In order to safely protect the components disposed therein from the external environment, the housing 121 may be formed of a material that is corrosion-resistant and lightweight. For example, the housing 121 may be formed of plastic, but is not necessarily limited to plastic, and may be made of any material capable of achieving the purposes described above. If necessary, the housing 121 may be formed of a composite material.

Further, the scanner body 120 may include at least one camera 122 in the housing 121. The camera 122 may have a lens that is capable of receiving light entering through the tip 110. The camera 122 may transmit the received light to an imaging sensor (not shown) electrically connected to the camera 122 to generate image data. The imaging sensor may be, for example, a CCD sensor or a CMOS sensor, but is not limited thereto. The image data may be two-dimensional planar data including a plurality of pixels. The camera 122 may have a single-cam structure with a single camera 122a or 122b. Furthermore, the camera 122 may have a multi-cam structure with two or more cameras, such as the first camera 122a and the second camera 122b.

Further, the scanner body 120 may include a light projector 123. The light projector 123 may be formed on one side of the camera 122, and the light projector 123 may generate light and emit the light toward the outside of the scanner. The light projector may be disposed at various locations on the scanner body 120. The light generated by the light projector 123 may be output to the outside via the optical member 113 and the first opening 111. The output light may reach the surface of a scan target, be reflected, and be received in the camera 122 embedded in the scanner body 120.

The light output from the light projector 123 may be light in various wavelength ranges. The light output from the light projector 123 may be structured light, and the structured light may be generated by passing light generated from a light source in the light projector 123 through a pattern mask or through an electronic array device (a digital micromirror device). The structured light may have a regular pattern. For example, the pattern of the structured light may be, but is not limited to, a vertical stripe pattern or a horizontal stripe pattern. The image data of the scan target, which is acquired with the irradiated structured light, has depth information, so that the two-dimensional image data may be converted into a three-dimensional model.

The scanner body 120 may include an attachment/detachment surface 124 formed at one end thereof so as to be coupled to the tip 110. The attachment/detachment surface 124 may be brought into contact with a portion of the tip 110, and the attachment/detachment surface 124 may be brought into contact with the tip 110 as the scanner body 120 is inserted through the second opening 112 of the tip 110. In this way, the tip 110 and the scanner body 120 may be coupled to each other by the attachment/detachment surface 124 to form the integrated scanner 100.

An attachment/detachment confirmation means 125 may be formed on the attachment/detachment surface 124 so as to detect the attachment or detachment of the tip 110. The attachment/detachment confirmation means 125 may detect whether the tip 110 is stably attached (coupled) to the scanner body 120. Based on the attachment or detachment of the tip 110, the attachment/detachment confirmation means 125 may provide a controller (not shown), which will be described later, with attachment/detachment information for updating usage information of the tip 110. For example, the attachment/detachment information may refer to an attachment state in which whether the tip 110 is attached to or detached from the scanner body is confirmed. Accordingly, when the attachment/detachment confirmation means 125 detects that the tip 110 is attached, the controller may operate to update the usage information of the tip 110. In this case, any means capable of detecting whether the tip 110 is stably attached to the scanner body 120 may be used as the attachment/detachment confirmation means 125. For example, the attachment/detachment confirmation means 125 may be a means for confirming attachment and detachment based on a change in pressure, or a means for confirming attachment and detachment based on light detection. More specifically, the attachment/detachment confirmation means 125 may be at least one of a pressure sensor, which is pressed by the tip 110 to recognize the attachment of the tip 110, and a photosensor, which recognizes the attachment of the tip 110 by light detection. The photosensor may be at least one of a proximity sensor, a micro photosensor, a beam sensor, and an illumination sensor, but not limited thereto.

Figure 4:
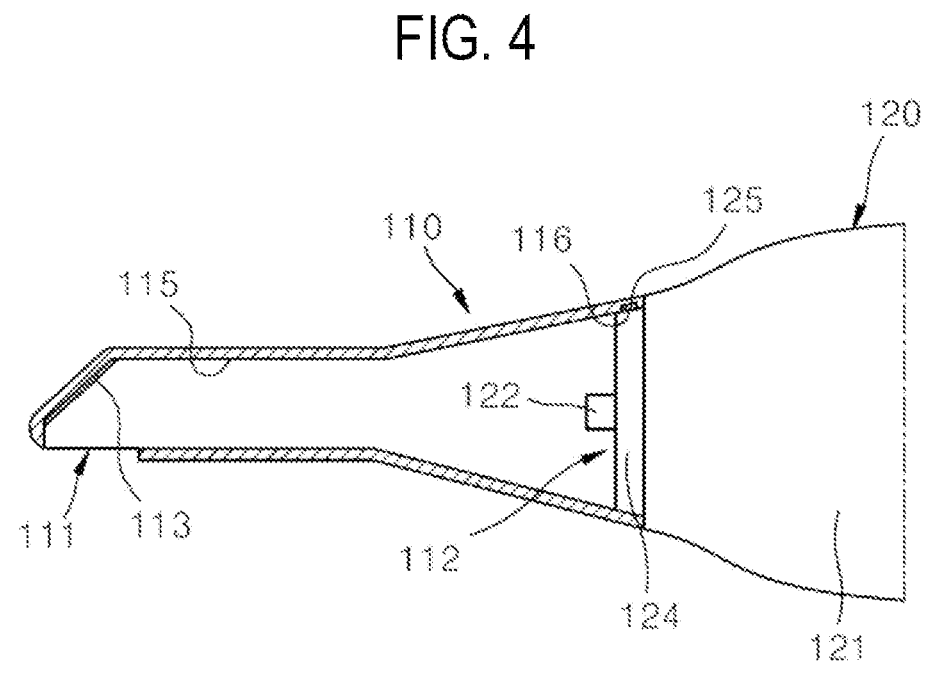

FIG. 4 illustrates a cross-sectional view of the tip 110 and the scanner body 120 coupled to each other in an image processing apparatus according to the first embodiment of the present disclosure.

The coupling of the tip 110 and the scanner body 120 will be further described with reference to FIG. 4. The attachment/detachment confirmation means 125 of the scanner body 120 may be received in the receiving groove 116 formed in an inner side of the tip 110. For example, the attachment/detachment confirmation means 125 may be pressed toward the attachment/detachment surface 124 during coupling of the tip 110 to the scanner body 120. When the attachment/detachment confirmation means 125 is disposed at a location corresponding to the receiving groove 116, the attachment/detachment confirmation means 125 may be received in the receiving groove 116, and may detect a pressure change at this time to confirm whether the tip 110 is properly attached to the scanner body 120. Further, the attachment/detachment confirmation means 125 may be received in the receiving groove 116 of the tip 110 to ensure that the tip 110 is attached in a correct location.

The foregoing embodiment describes a form in which the receiving groove 116 is formed in the tip 110 and in which the attachment/detachment confirmation means 125 is received in the receiving groove 116. However, the image processing apparatus of the present disclosure is not necessarily limited thereto, and a groove may be formed in the scanner body 120, and the attachment/detachment confirmation means 125 may be provided in the groove of the scanner body 120.

The foregoing has been described using a pressure sensor as an example, but the present disclosure is not limited thereto. Even when a photosensor or another sensor is used as the attachment/detachment confirmation means 125, whether the tip 110 is properly attached may also be confirmed by an operation corresponding to the sensor.

Hereinafter, a detailed description will be made of an image processing apparatus according to a second embodiment of the present disclosure, including an identifier element which provides unique information for identifying the type of the tip 110.

Figure 5A:
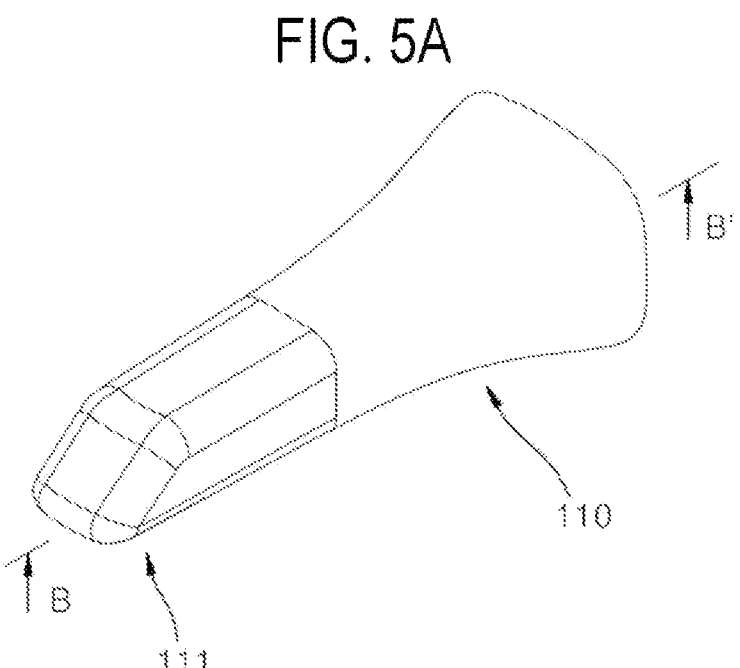
Figure 5B:
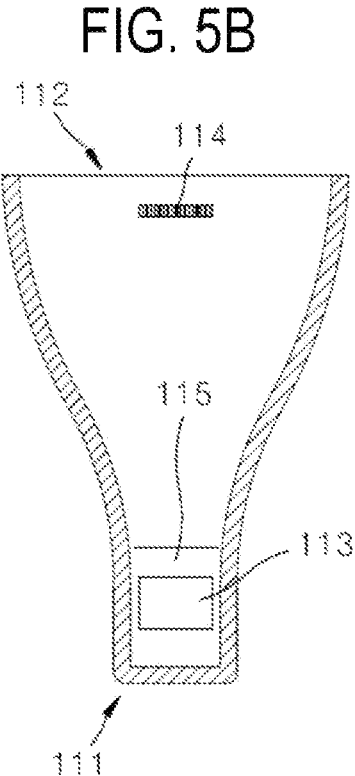
Figure 5C:
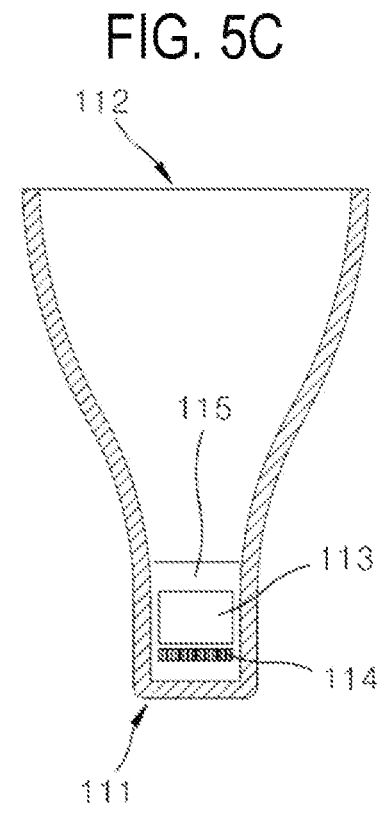

FIGS. 5A, 5B, and 5C illustrate a perspective view (FIG. 5A) and cross-sectional views (FIGS. 5B and 5C) taken along line B-B' of the tip 110 in the image processing apparatus according to the second embodiment of the present disclosure. Referring to FIG. 5B, the tip 110 of the image processing apparatus according to the second embodiment of the present disclosure may include an identifier 114, which has unique information on one side thereof. The identifier 114 corresponds to a mark that distinguishes a particular object from another object. More specifically, the identifier 114 may have unique information of the tip 110. The unique information may refer to information for individually identifying tips 110, and may be, for example, the manufacturer, serial number, manufacturing number, manufacturing date, etc. of the tip 110. In order to individually identify the tips 110, the tips 110 having different identifiers 114 have different pieces of unique information. The identifier 114 may be any representation means that contains the unique information of the tip 110. For example, the identifier 114 may be, but is not limited to, a bar code, a QR code, a serial number, or the like. When the identifier 114 is detected by the camera 122, the controller may operate to update the usage information of the tip 110.

Hereinafter, a location wherein the identifier 114 is disposed will be described.

The identifier 114 may be disposed on one surface of the tip 110. For example, the identifier 114 may be disposed on the inner surface 115 of the tip 110. When the identifier 114 is disposed on the inner surface 115 of the tip 110, a user may detect the identifier 114 through the camera 122 before coupling the tip 110 to the scanner body 120. In order to facilitate detection of the identifier 114 by the camera 122, the identifier 114 may be disposed at a location adjacent to the second opening 112 side.

The forgoing describes the identifier 114 as being disposed at a location adjacent to the second opening 112 side, but the present disclosure is not necessarily limited thereto. Referring to FIG. 5C, the identifier 114 may be disposed at a location adjacent to the first opening 111 side.

Disposing the identifier 114 on the inner surface 115 may minimize exposure of the tip 110 to contamination resulting from being inserted into and withdrawn from a patient's oral cavity. The outer surface (not shown) of the tip 110 may become contaminated or worn by contact with the inside of the patient's oral cavity, but the inner surface 115 of the tip 110 is protected from contamination or wear, and thus the identifier 114 may also be protected from contamination or wear.

Hereinafter, the arrangement relationship between the identifier 114 and the optical member 113 will be described.

Figure 6:
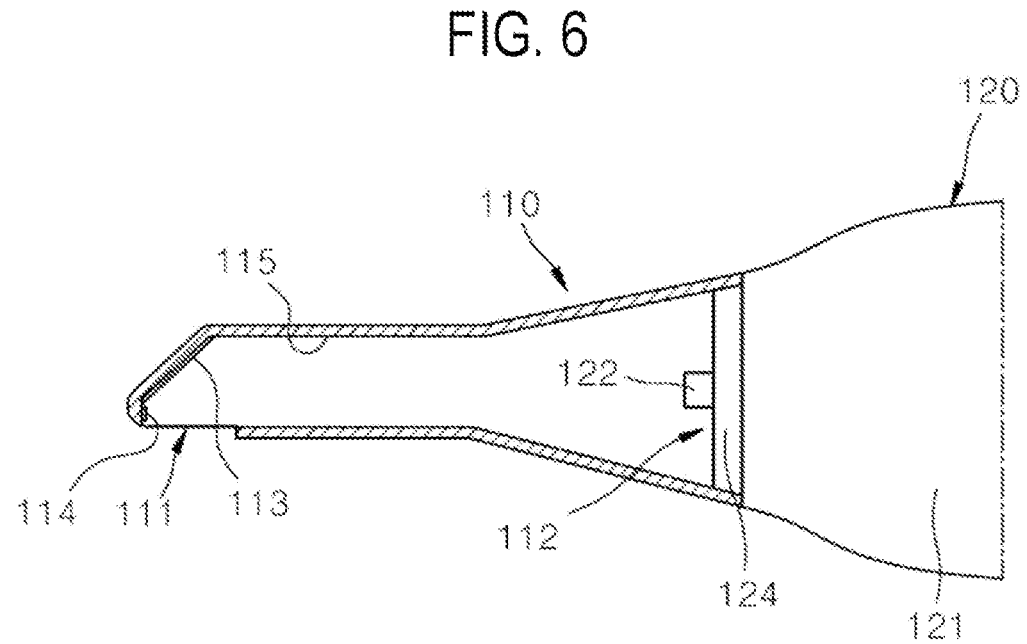
FIG. 6 illustrates a cross-sectional view of a tip and a scanner body coupled to each other in an image processing apparatus according to a third embodiment of the present disclosure.

FIG. 6 illustrates a cross-sectional view of a tip and a scanner body coupled to each other in an image processing apparatus according to a third embodiment of the present disclosure. Referring to FIG. 6, the identifier 114 may be disposed on one side of the optical member 113. For example, the one side of the optical member 113 on which the identifier 114 is disposed may be the first opening 111 side, but is not necessarily limited thereto. Accordingly, the camera 122 of the scanner body 120 may receive light refracted or reflected from the optical member 113, together with an image of the identifier 114. That is, the identifier 114 may be disposed within an angle of view of the camera 122 formed in the scanner body 120 when the tip 110 is coupled to the scanner body 120, and may be disposed at one outer side from the periphery of the optical member 113.

With the identifier 114 disposed on one side of the optical member 113, the user may ensure that the identifier 114 is automatically detected by the camera 122 after coupling of the tip 110 to the scanner body 120. When the identifier 114 is detected by the camera 122, the controller may operate to update usage information of the tip 110. Alternatively, after the identifier 114 is detected by the camera 122 and when a scanning operation ends, the controller may operate to update the usage information of the tip 110. When the scanner is powered on, the camera 122 is turned on, and camera 122 may automatically detect the identifier 114, thereby preventing omission of updating the usage information of the tip 110.

Hereinafter, a detailed description will be made of the process in which the camera 122 detects the identifier and adjusts the Region of Interest (ROI) to acquire image data for forming a three-dimensional model.

Figure 7:
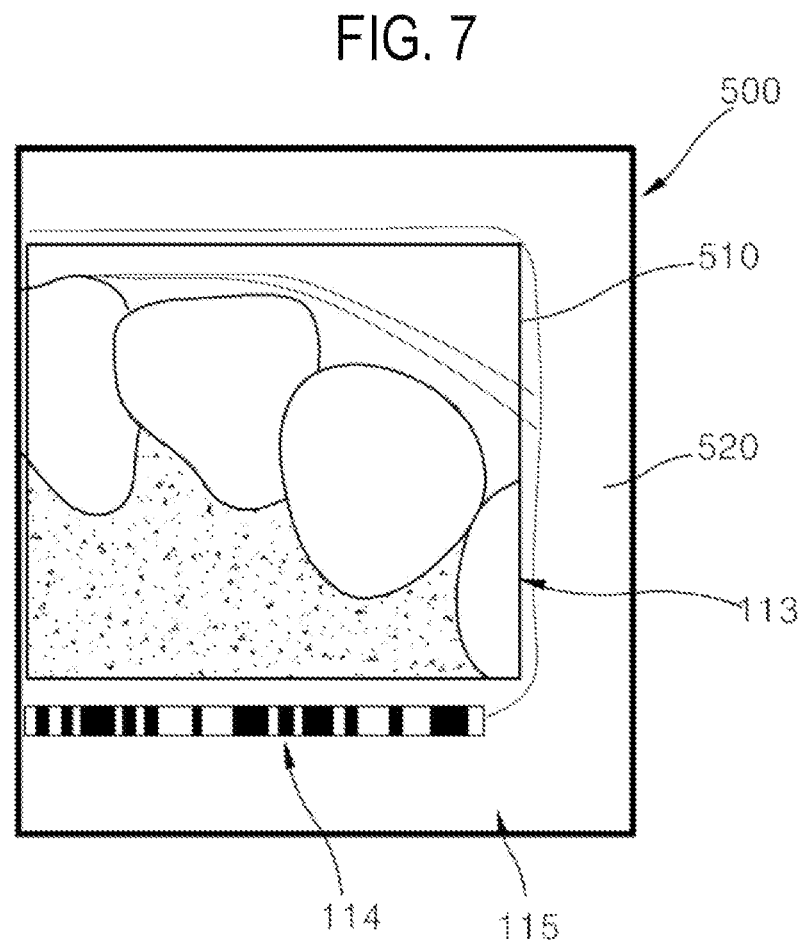
FIG. 7 is a view illustrating a time point of detecting an identifier in an image processing apparatus according to a third embodiment of the present disclosure.
Figure 8:
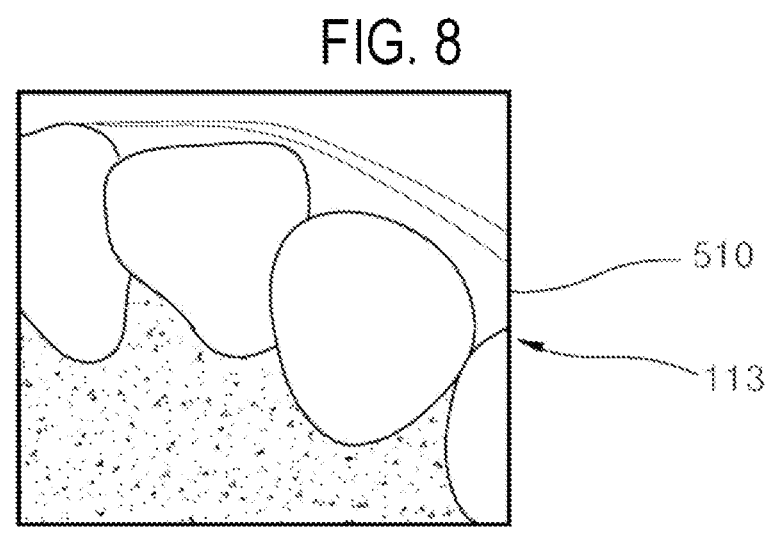

FIG. 7 is a view illustrating a time point of detecting an identifier in an image processing apparatus according to a third embodiment of the present disclosure. FIG. 8 is a view illustrating a time point of performing a scanning process in the image processing apparatus according to the third embodiment of the present disclosure. In FIGS. 7 and 8, portions indicated by thick solid lines are portions of which image data is acquired by the camera 122.

Referring to FIG. 7, image data acquired by the camera 122 is shown. Image data acquired at the time point of detecting the identifier 114 has an input area 500 corresponding to the angle of view of the camera 122. The input area 500 may include a first area 510 and a second area 520. The first area 510 is an area formed by receiving light introduced into the tip 110 in the camera through the optical member 113 in the input areas 500 corresponding to the angle of view of the camera. More specifically, the first area 510 refers to an area where light introduced into the tip 110 is reflected through the optical member 113 and received in the camera 122, and formed as image data.

The second area 520 may be the remaining area of the input area 500 other than the first area 510, or an area that does not include the first area 510. More specifically, the second area 520 refers to an area of the input area 500 corresponding to the angle of view of the camera, wherein light reflected from the inner surface 115 of the tip 110 is directly received in the camera 122 without going through the optical member 113 and formed as image data. More specifically, the second area 520 may refer to an area formed by excluding the first area 510 from the generated image data. The angle of view of the camera includes not only the optical member 113, but also a portion of the inner surface 115 of the tip adjacent to the optical member 113. In other words, the angle of view of the camera may include the optical member 113 and the identifier 114 together.

Meanwhile, the identifier 114 may be located in the second area 520 formed outside the first area 510 in the image data. The identifier 114 may be detected in the second area 520, i.e., outside the first area 510. More specifically, the region of interest (ROI) in the process of detecting the identifier 114 may be the entire input area 500, including the first area 510 and the second area 520, or may include only the second area 520.

Referring to FIG. 8, image data acquired by the camera 122 is shown. Image data acquired at the time of performing a scanning process may be image data acquired after the region of interest (ROI) is adjusted. For example, when the scanner body 120 performs the scanning process regarding a scan target, the region of interest (ROI) may be adjusted to the first area 510. At this time, only image data of the scan target, received through the optical member 113, may be converted into a three-dimensional model. Since the region of interest (ROI) when performing the scanning process is limited to the first area 510, the identifier 114 disposed in the second area 520 is not converted into a three-dimensional model.

Figure 9A:
FIGS. 9A and 9B illustrate an example of an identifier in an image processing apparatus according to a fourth embodiment of the present disclosure.
Figure 9B:
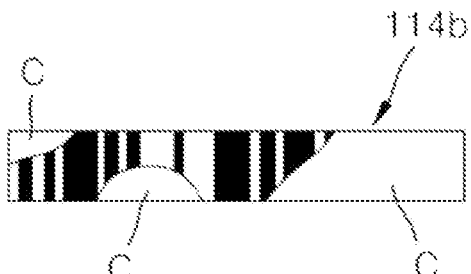

As described above, the region of interest in the process of detecting the identifier is different from the region of interest in the process of performing the scanning process, and thus it is possible to prevent an inaccurate three-dimensional model from being generated due to the conversion of the identifier 114 into a three-dimensional model FIGS. 9A and 9B illustrate an example of an identifier in an image processing apparatus according to a fourth embodiment of the present disclosure.

Referring to FIGS. 9A and 9B, the identifier 114 may be formed of a special printing material and may undergo discoloration in a predetermined environment. For example, the identifier 114 may be printed with an ink that brightens under high temperature and pressure, and in the operating environment of the image processing apparatus according to the present disclosure, the pattern of the identifier 114 may gradually fade over time. Thus, when a predetermined time elapses, the identifier 114 has a discolored portion C, and when the discolored portion C occurs over a predetermined range, the camera is unable to detect the identifier 114. Accordingly, when the identifier 114 is unable to be detected, the image processing apparatus may induce the user to replace the tip 110 by, for example, giving the user a notification. When necessary, the image processing apparatus may induce the user to replace the tip 110 by restricting the scanning process of the image processing apparatus from being performed when the tip 110 is not detected by the identifier 114.

Hereinafter, an embodiment including the identifier 114 and attachment/detachment confirmation means 125 together will be described.

Figure 10:
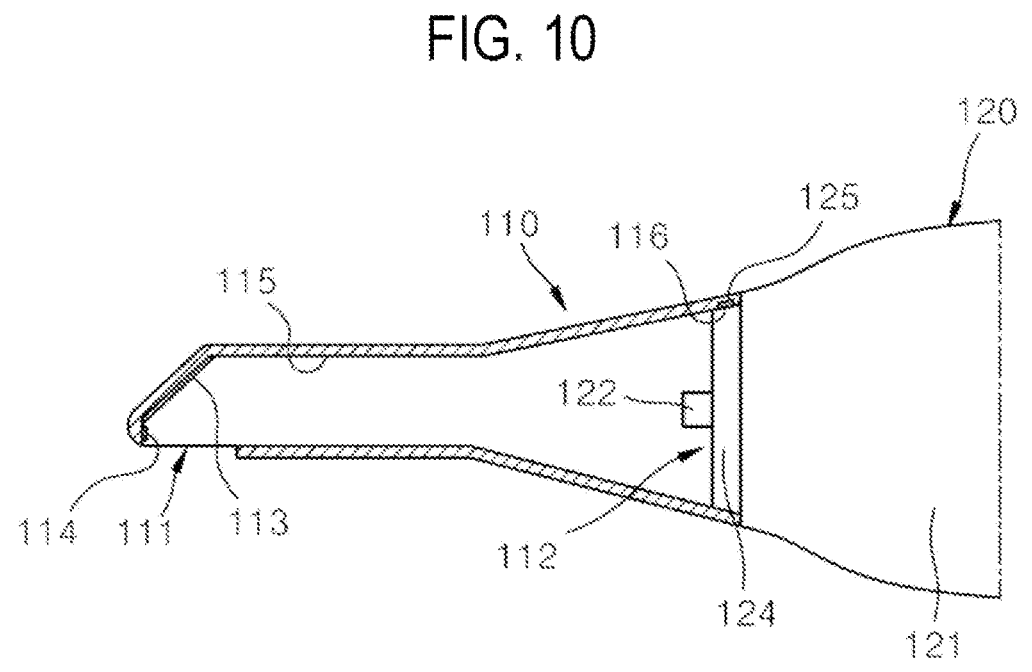

FIG. 10 illustrates a cross-sectional view of a tip 110 and a scanner body 120 coupled to each other in an image processing apparatus according to a fifth embodiment of the present disclosure. Referring to FIG. 10, an identifier 114 may be disposed at the tip 110, and an attachment/detachment confirmation means 125 may be formed on the scanner body 120. With such a configuration, the attachment/detachment confirmation means 125 may have both the advantage of easily confirming whether the tip 110 and the scanner body 120 are properly coupled and the advantage of recognizing the identifier 114 to separately update usage information of each tip 110. By measuring the elapsed time from the detachment to the reattachment of the tip 110 through an operation of the attachment/detachment confirmation means 125, it is possible to determine whether the tip 110 has been cleaned and sterilized, and to optionally update usage information for the tip 110. The process of determining whether the tip 110 has been cleaned and sterilized and optionally updating the usage information of the tip 110 will be described later.

Hereinafter, the configuration of a controller 200 of an image processing apparatus according to the present disclosure will be described.

Figure 11A:
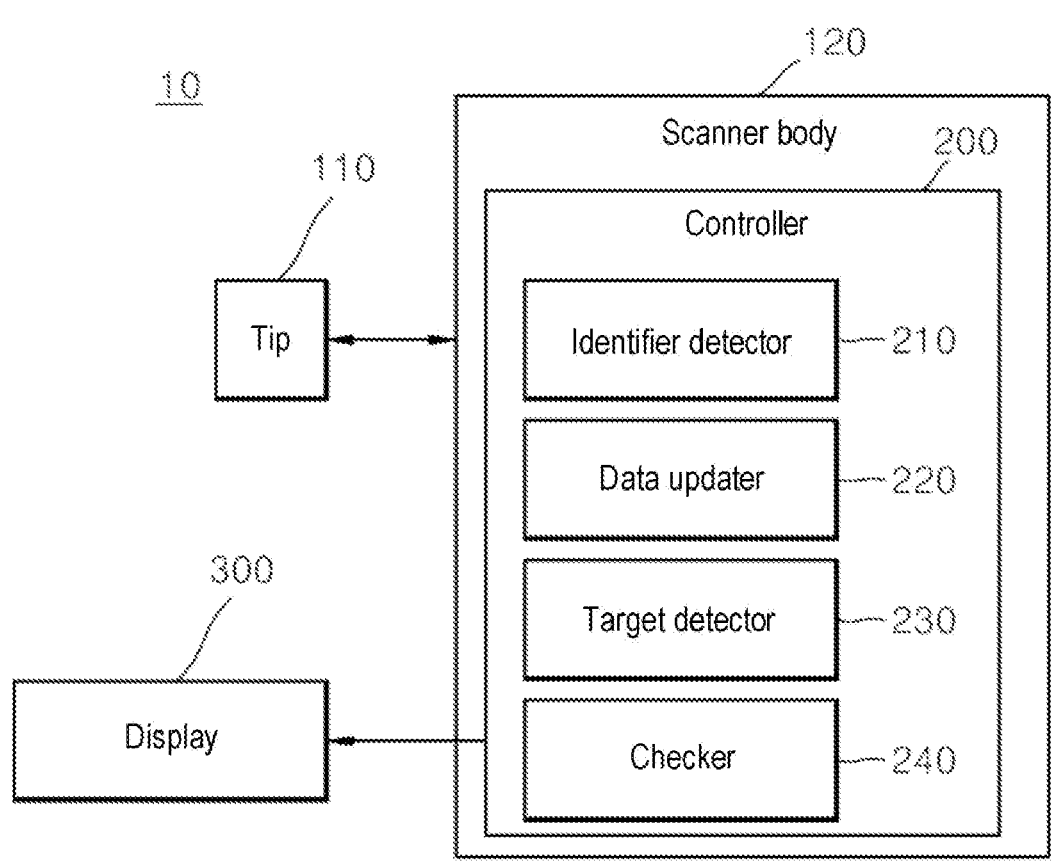
FIGS. 11A and 11B are schematic views of a configuration of an image processing apparatus according to the present disclosure.
Figure 11B:
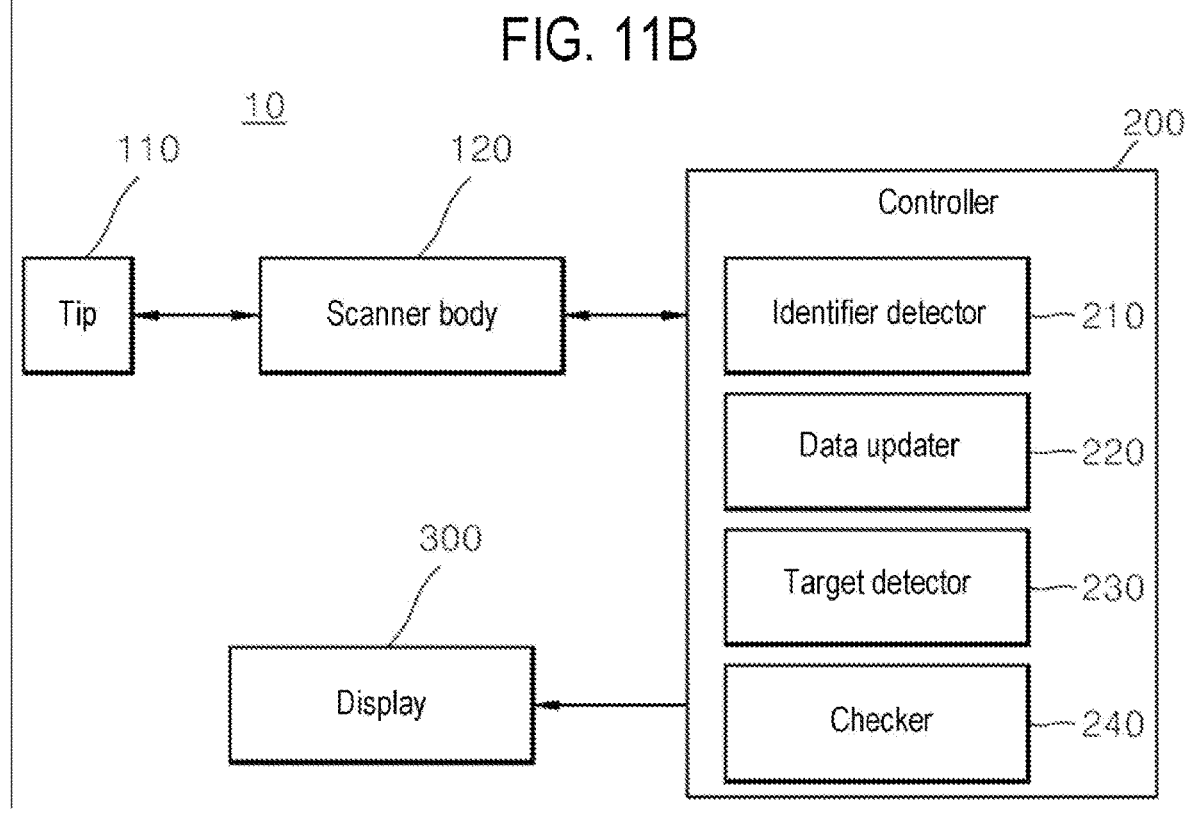

FIGS. 11A and 11B are schematic views of a configuration of an image processing apparatus according to the present disclosure.

Referring to FIGS. 11A and 11B, the controller 200 may detect an identifier, and may update usage information of the tip 110. The controller 200 may function as a processor embedded in the scanner body 120, as shown in FIG. 11A, or may be formed in a structure in which the controller 200 is physically separate from the scanner body 120, as shown in FIG. 11B. That is, the location where the controller 200 is formed may be inside or outside the scanner body 120, and the formation location is not limited.

Further, the controller 200 may include an identifier detector 210 for extracting unique information of the tip 110 from the identifier 114, and a data updater 220 for selectively updating usage information of the tip 110 assigned to the unique information.

The identifier detector 210 may detect the identifier 114 from light received by the camera 122. The identifier detector 210 may read, from generated image data, a portion in which the identifier 114 is input, and may load, into a system, the unique information of the tip 110 that the identifier includes. The identifier detector 210 may load individualized unique information for each tip.

When the unique information included in the identifier is loaded by the identifier detector 210, usage information corresponding to the unique information may be loaded therewith. The usage information may be records stored on a local storage device and loaded by the identifier detector 210, or records stored on a cloud storage and loaded. The usage information corresponding to the above-described unique information may be whether the tip is discolored, the number of times the tip has been used, etc. Among these, the number of uses may be used as the most objective indicator of the usage information of the tip. The number of uses expresses the number of times the corresponding tip 110 has performed scanning, and the number of uses is related to the wear of the tip, and thus is directly related to patient hygiene.

The data updater 220 may selectively update the usage information of the tip. In this case, "selectively" updating the usage information of the tip may refer to that the data updater 220 detects the identifier once and increments information about the number of uses by one as a one-time scanning process ends. Alternatively, "selectively" updating the usage information of the tip may refer to that depending on the type of scan target, the data updater 220 may or may not increment the number of uses by one after the end of the one-time scan process. The process of selectively updating the usage information of the tip depending on the type of scan target and/or the elapsed time between the detachment and reattachment of the tip from and to the scanner body will be described later.

Further, the data updater 220 may determine through the aforementioned attachment/detachment confirmation means 125 that when the tip 110 has been detached from and then attached to the scanner body 120, a scan has been performed and a sterilization operation for the tip 110 has been performed, and may update the usage information of the tip 110. Accordingly, the attachment/detachment confirmation means 125 provides additional parameters that may be used to update the usage information of the tip 110 in conjunction with the identifier 114.

The process of detecting the identifier 114 may be performed by the camera 122 formed in the scanner body 120, immediately following an on/off operation of the scanner power. Alternatively, the process of detecting the identifier 114 may be performed by the operation of the camera 122 after the attachment of the tip 110 is detected by the attachment/detachment confirmation means 125.

In the case of an embodiment that includes only the attachment/detachment confirmation means 125 without the identifier 114, the usage information of the tip may be updated (e.g., incrementing the number of uses of the tip by one) as the attachment of the tip 110 is detected by the attachment/detachment confirmation means 125 and a one-time scanning process ends. Alternatively, depending on the type of scan target, the data updater 220 may or may not increment the number of uses by one after the end of the one-time scanning process. For example, the attachment/detachment confirmation means 125 may provide the controller 200 with attachment/detachment information indicating whether the tip 110 has been detached from or attached to the scanner body 120, based on the attachment and detachment of the tip 110, and the controller may confirm whether the tip is attached, based on the attachment/detachment information. Thus, the controller 200 may determine the attachment or detachment of the tip, based on the attachment/detachment information provided by the attachment/detachment confirmation means 125, and may update the usage information of the tip 110.

Hereinafter, the process of selectively updating the usage information of the tip 110 depending on the type of scan target will be described in detail.

In an image processing apparatus 10 according to the present disclosure, the controller 200 may further include a target detector 230 configured to detect the type of scan target. The target detector 230 may detect what kind of object a scanned scan target is. For example, the scan target may be the actual inside of a patient's oral cavity, or a plaster cast obtained by taking an impression. The target detector 230 may analyze information, including color, texture, reflectivity, etc. of the scan target from light received in the camera 122 to determine whether the scan target is an oral cavity or a plaster cast.

The target detector 230 may operate in conjunction with the data updater 220. The data updater 220 operating in conjunction with the target detector 230 may update the number of uses of the tip depending on the type of scan target. For example, when a scan target is the actual oral cavity of a patient, the tip 110 may be inserted into and withdrawn from the oral cavity of the patient, and thus the surface thereof is likely to be contaminated by foreign matter, including the patient's saliva. In this case, the tip 110 should be separated from the scanner body 120 and cleaned and sterilized. On the other hand, when a scan target is a plaster cast, no contamination of the tip 110 occurs, so cleaning and sterilization are not necessary, and the tip 110 does not need to be detached. However, when the scan target is changed from the plaster cast to the patient's actual oral cavity, cleaning and sterilization of the tip 110 may be required.

Accordingly, the data updater 220 operating in conjunction with the target detector 230 may detect the identifier 114 of the tip 110 to acquire unique information of the tip, and may update usage information assigned to the unique information in the case in which the scan target, when scanned, is the oral cavity. Further, when the usage information exceeds a predetermined threshold value, the image processing apparatus may generate a guidance message or a warning signal (sound, lighting, vibration, or the like) indicating that the tip 110, which has the unique information is due for replacement, thereby informing a user of the replacement cycle of the tip. For example, the aforementioned usage information may be the number of times the tip 110 has been used.

Further, to protect a patient from an unsanitary scanning environment, scanning operations of the image processing apparatus may be limited by determining whether the tip 110 is sterile. For example, the controller 200 may further include a checker 240 that detects whether the tip 110 is attached to or detached from the scanner body 120. The checker 240 may detect the attachment or detachment of the tip 110 through the attachment/detachment confirmation means 125. The checker 240 may acquire an elapsed time from detachment of the tip 110 from the scanner body 120, after the scanner 100 scans the scan target, to reattachment of the tip 110 to the scanner body 120. The elapsed time may be used as an indicator indicating that the tip 110 has been removed from the scanner body 120 and cleaned and sterilized over a predetermined time.

When the elapsed time is below a threshold value and when the scan target is the oral cavity, it may be determined that sufficient cleaning and sterilization has not been performed. For example, when the elapsed time is less than the minimum time required for sterilization cleaning, subsequent scanning operations of the image processing apparatus 10 may be restricted, or a user may be notified. As such, the image processing apparatus according to the present disclosure may use the elapsed time to control the operation of the image processing apparatus 10 and may provide a hygienic scanning environment to the patient.

Further, when the elapsed time is less than the threshold value, it may be determined that the user has performed an unnecessary attachment/detachment action, and the data updater 220 may not update (increment) information about the number of uses. For example, when the elapsed time is within 5 seconds, it may not be determined that the tip was used. Only when the elapsed time is greater than or equal to the threshold value, the data updater 220 may update (increment) the information about the number of uses.

The unique information of the tip, the usage information of the tip, the image data having an input area, the guidance message, and the like, which have been described above, may be visually displayed through a display 300. A user of the image processing apparatus according to the present disclosure can easily grasp the unique information of the tip, the usage information of the tip, the image data, the guidance message, and the like through the display 300.

Hereinafter, displaying the unique information of the tip, the usage information of the tip, etc. through the display 300 will be described in more detail.

Figure 12:
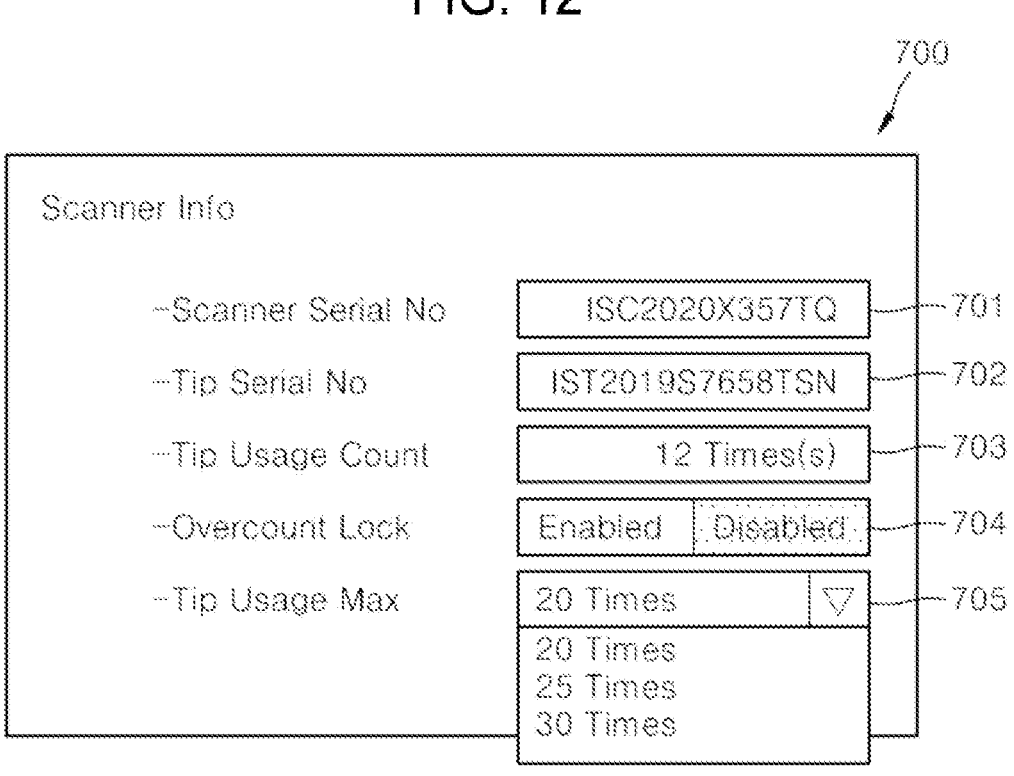

FIGS. 12 and 13 illustrate a process of updating usage information of a tip in an image processing apparatus according to the present disclosure.

Referring to FIG. 12, information about the image processing apparatus may be displayed on a user interface 700. For example, the user interface 700 may display scanner information 701, tip information 702, tip usage information 703, excessive scanning limit 704, and tip usage upper limit 705. The scanner information 701 displayed on the user interface 700 may be a model name of a connected scanner. As shown, the scanner information 701 may be displayed as a type of serial number, but may also be displayed simply as a product name. The user interface 700 may display unique information extracted from an identifier in the tip information 702, and the unique information of a tip may include the manufacturer, model name, serial number, etc. of the tip. Thus, the tip information 702 as shown in FIG. 12 is an example of the unique information of a tip, and the unique information of a tip may be visually displayed in various forms on the user interface 700.

The user interface 700 may display the tip usage information 703. For example, the tip usage information 703 may include the number of times a tip has been used. As described above, the value of the tip usage information 703 may be updated each time the tip usage information is updated. For example, the tip usage information 703 may be incremented by 1 after scanning a scan target.

Further, the user interface 700 may restrict the operation of a scanner under predetermined conditions, including the excessive scanning limit 704. For example, the scanner may be restricted from operating when the value of the tip usage information 703 exceeds the maximum tip usage count 705. However, in some cases, the function of restricting the operation of the scanner may be enabled or disabled by the user.

Further, the user interface 700 includes the maximum tip usage count 705, and a user can adjust the maximum tip usage count 705. However, the maximum tip usage count 705 may be adjusted to the extent that a hygienic environment can be provided to the user and a patient.

Referring to FIG. 13, the user interface 700 may output a notification message 706 when the value of the tip usage information 703 exceeds the maximum tip usage count 705. For example, when the maximum tip usage count 705 is 20 and when the value of tip usage information 703 is 21, the notification message 706 may recommend the user to use a new tip. The notification message 706 may be displayed before or after the scanning process of the scanner. As the notification message 706 is displayed, the user can easily check the tip usage information and can provide a hygienic treatment environment to the patient by periodically replacing a tip.

Although not shown in FIGS. 12 and 13, the user interface 700 may further display an elapsed time from the detachment to the reattachment of a tip. Further, when the elapsed time is less than a predetermined time, the user interface 700 may additionally display a message recommending sufficient cleaning and sterilization of the tip. In accordance with the foregoing, the user can easily visually recognize pieces of usage information of the tip through the user interface 700.

Hereinafter, an image processing method according to the present disclosure will be described in detail. When a description overlaps with the foregoing detailed description of the image processing apparatus, the description will be made briefly or omitted.

Figure 14:
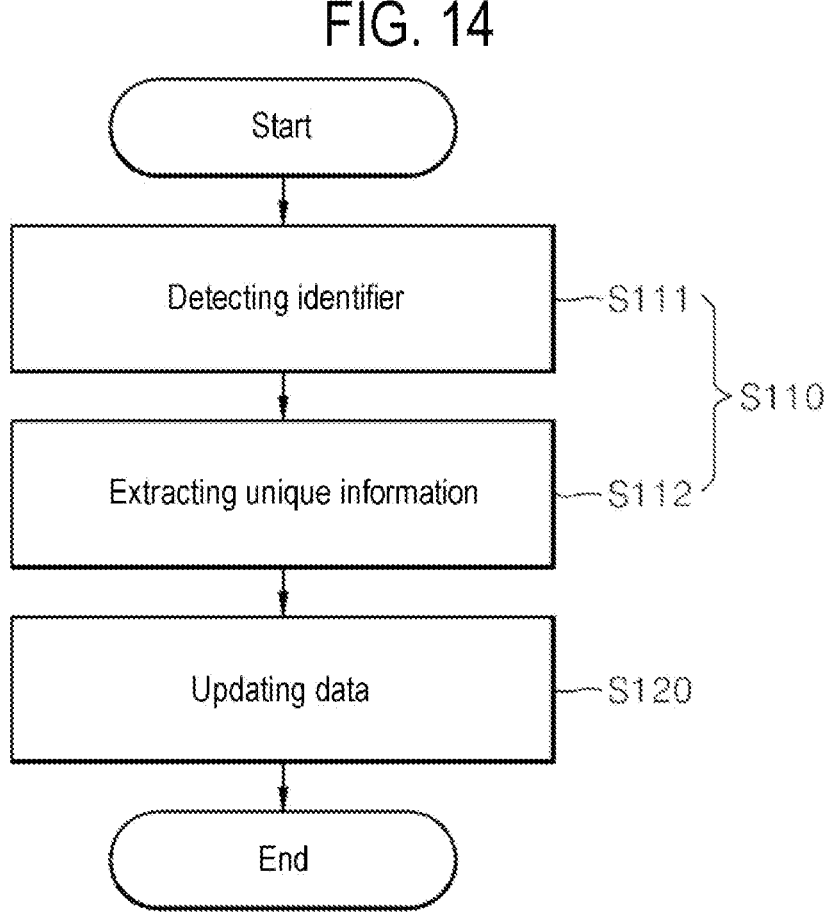
FIG. 14 is a flowchart of an image processing method according to a first embodiment of the present disclosure.

FIG. 14 is a flowchart of an image processing method according to a first embodiment of the present disclosure.

Referring to FIG. 14, an image processing method according to the present disclosure may include a unique information identification step S110 of identifying unique information of a tip detachably coupled to one end of a scanner body, and a data updating step S120 of updating usage information of the tip assigned to the unique information identified in the unique information identification step.

First, when the power of an image processing apparatus is turned on, a camera embedded in the scanner body identifies unique information of a tip (S110). Identifying the unique information may be interpreted in various ways, but in an example, may imply detecting an identifier attached to one surface of the tip and extracting the manufacturer, model name, etc. of the tip. In this case, the identifier including the unique information of the tip may be formed to be disposed on an inner surface of the tip, and the identifier may be photographed by the camera of the scanner body.

The unique information identification step S110 may include an identifier detection step S111 of detecting an identifier present in an input area, and a unique information extraction step S112 of extracting the unique information of the tip from the identifier acquired in the identifier detection step S111.

In the identifier detection step S111, a controller may detect an identifier including unique information of the tip. The identifier may be formed to be disposed at a specific location on the tip. For example, the identifier may be formed to be disposed on the outer side of the periphery of an optical member to be described below. However, the location of the identifier is not necessarily limited thereto, and the identifier may be disposed at any location that is within the angle of view of the camera embedded in the scanner body The tip may form a communicating structure by a first opening formed at one end and a second opening formed at the other end. Further, the tip may have an inner surface formed by the communicating structure, and the tip may include an optical member on the inner surface. When light reflected from the surface of a scan target is introduced into the tip, the optical member may refract or reflect the light toward the camera.

The camera embedded in the scanner body may receive light, and an imaging sensor electrically connected to the camera may generate image data from the light. In this case, the image data has an input area corresponding to the angle of view of the camera. The input area may include a first area and a second area. The first area is an area of the image data, generated by receiving light introduced from outside the tip in the camera through the optical member. The second area refers to the remaining area of the image data, generated by receiving the light reflected from the inner surface of the tip in the camera without going through the optical member, and the second area is the remaining area other than the first area in the input area. The identifier may be disposed on one side of the optical member. For example, the identifier may be located in the second area formed outside the first area in the image data. When detecting the identifier, the camera's region of interest (ROI) includes only the second area, or corresponds to the input area range that includes the first area and the second area, and when performing the scanning process, the camera's ROI corresponds to only the first area. As the identifier is located in the second area, the identifier does not correspond to the camera's region of interest during the scanning process, and therefore is not converted into a three-dimensional model. Accordingly, the image processing method according to the present disclosure may prevent an inaccurate three-dimensional model from being generated due to the conversion of the identifier into a three-dimensional model, and may reliably provide unique information.

As described above, in an identifier detection step S111, the controller may detect the identifier through the image data acquired from the camera. For example, the identifier may be at least one of a bar code, a QR code, or a serial number, but is not limited thereto, and may take any form having unique information of the tip.

Then, in the unique information extraction step S112, the controller extracts the unique information of the tip from the identifier. For example, the unique information of the tip may be at least one of a manufacturer, a serial number, a manufacturing number, and a manufacturing date of the tip, but is not limited thereto.

After the unique information identification step S110 including the identifier detection step S111 and the unique information extraction step S112 is performed as described above, in the data updating step S120, the controller may update usage information of the tip. More specifically, the data updating step S120 may be a step in which the controller detects the identifier once and increments information about the number of uses of the tip by one as a one-time scanning process ends.

Hereinafter, an image processing method according to a second embodiment of the present disclosure will be described.

Figure 15:
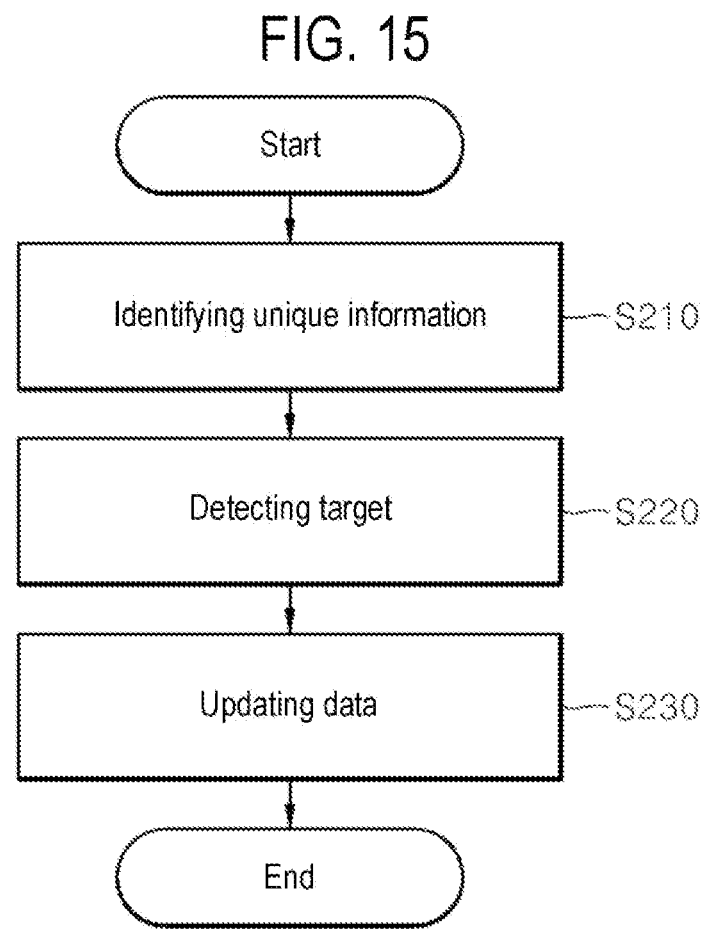
Figure 16:
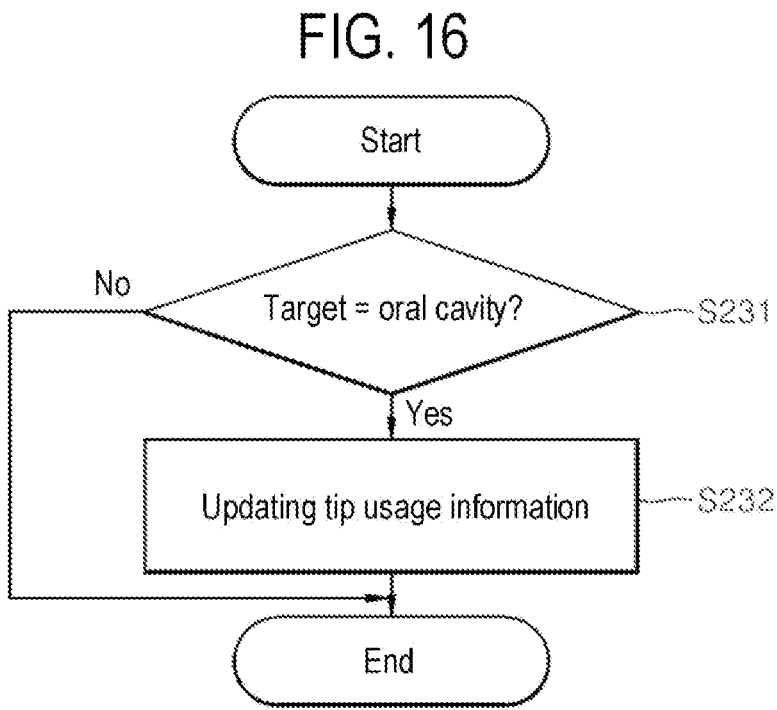
FIG. 16 is a flowchart of a data updating step in an image processing method according to the second embodiment of the present disclosure.

FIG. 15 is a flowchart of the image processing method according to the second embodiment of the present disclosure, and FIG. 16 is a flowchart of a data updating step in the image processing method according to the second embodiment of the present disclosure.

Referring to FIG. 15, the image processing method according to the second embodiment of the present disclosure may include a unique information identification step S210 and a data updating step S230 which are identical to those of the image processing method according to the first embodiment described above. However, the image processing method according to the second embodiment of the present disclosure may further include a target detection step S220 of detecting a scan target scanned by a scanner body, before the data updating step S230.

The target detection step S220 may be a step of detecting what kind of object the scanned scan target is. For example, the scan target may be the actual oral cavity of a patient, or a plaster cast obtained by taking an impression of the patient's oral cavity. Through the target detection step S220, usage information of a tip may be selectively updated depending on the type of scan target.

Referring to FIG. 15, when the unique information identification step S210 of identifying unique information of the tip is performed, and when a scanning step (not shown) of scanning the scan target is performed, the type of the scan target may be detected from image data in the target detection step S220. Referring to FIG. 16, the data updating step S230 may include a scan target determination step S231 and a usage information updating step S232. In the scan target determination step S231, the controller may determine that the tip has been substantially used when the scan target is the actual oral cavity of the patient. When the type of scan target is determined in the scan target determination step S231, the usage information updating step (S232) of selectively updating usage information of the tip may be performed. For example, when the scan target is determined to be the patient's actual oral cavity, the usage information of the tip may be updated (incremented). On the other hand, when the scan target is a plaster cast, the usage information of the tip may not be updated because cleaning and sterilization processes are not required. By selectively updating the usage information depending on the detected type of scan target, it is possible to prevent the usage information of the tip from being updated unnecessarily.

The image processing method according to the first embodiment of the present disclosure and the image processing method according to the second embodiment of the present disclosure may further include an attachment/detachment confirmation step (not shown) in which an attachment/detachment confirmation means detects whether the tip is attached or detached. In the attachment/detachment confirmation step, whether the tip is stably coupled to the scanner body may be confirmed. The attachment/detachment confirmation means may be at least one of a pressure sensor, which is pressed by the tip to recognize the attachment of the tip, or a photosensor, which recognizes the attachment of the tip by light detection based on whether the tip is attached or not. Through the attachment/detachment confirmation step, whether the tip is stably attached to the scanner body may be confirmed.

Alternatively, in the image processing method according to the first embodiment of the present disclosure and the image processing method according to the second embodiment of the present disclosure, the unique information identification step may be replaced by the attachment/detachment confirmation step (not shown) of confirming whether the tip is attached to or detached from the scanner body. For example, when it is detected, in the attachment/detachment confirmation step, that the tip is detached and then reattached, in the data updating step S120, S230, the controller may increment the information of the number of uses of the tip by one.

Hereinafter, an image processing method according to a third embodiment of the present disclosure will be described.

FIG. 17 is a flowchart of the image processing method according to the third embodiment of the present disclosure.

Referring to FIG. 17, the image processing method according to the third embodiment of the present disclosure includes a unique information identification step S320 and a target detection step S340 which are identical to those of the image processing method according to the second embodiment of the present disclosure. However, the image processing method according to the third embodiment of the present disclosure may further include an attachment/detachment confirmation step S310 of detecting whether a tip is attached to a scanner body, and an elapsed time acquisition step S330 of acquiring an elapsed time from when a tip is detached from a scanner body after a scanner scans a scan target to when the tip is reattached to the scanner body. The elapsed time acquisition step S330 may be performed by detecting an attachment/detachment confirmation means in the attachment/detachment confirmation step S310. In the elapsed time acquisition step S330, a time when the tip is detached from the scanner body by the attachment/detachment confirmation means may configured to be a start time, and a time when the tip is reattached to the scanner body may be configured to be an end time. In the elapsed time acquisition step S330, the elapsed time between the start time and the end time may be acquired. The elapsed time may be acquired in seconds, and the elapsed time may be used as an indicator for determining whether the tip that performed the scan was cleaned and sterilized. The elapsed time may also be used as an indicator for determining that the tip is not in use and that the user has performed a habitual attachment/detachment behavior. For example, when the elapsed time is less than 5 seconds, it may be determined that the user has not used the tip for an oral scan. In this case, the controller may not update information about the number of uses.

The image processing method according to the third embodiment of the present disclosure may further include an operation control step S350 of controlling the operation of the image processing apparatus according to the type of scan target and the length of elapsed time. In the operation control step S350, the type of scan target detected through the target detection step S340 is determined (a scan target determination step S351).

After the scan target determination step S351 is performed, a usage information updating step S352 may be performed based on the determined type of scan target. In the usage information updating step S352, usage information of the tip may be selectively updated based on the type of scan target. For example, when the scan target is a plaster cast, no special cleaning and sterilization process is required even after the scanning process. Therefore, the cleaning and sterilization process for the tip cannot be forced for hygienic reasons. Accordingly, when the scan target is a plaster cast, the controller may not update the number of uses of the tip.

However, when the scan target is the oral cavity, the tip needs to be cleaned and sterilized, and the tip needs to be replaced when the oral cavity is scanned more than a predetermined number of times. Therefore, when the scan target is the oral cavity, the controller may update (increment) the information about the number of times the tip is used.

Further, when the scan target is the oral cavity, an elapsed time determination step S353 may be additionally performed to determine the elapsed time between the detachment and reattachment of the tip from and to the scanner body. In the elapsed time determination step S353, when the elapsed time acquired in the elapsed time acquisition step S330 is less than an elapsed time threshold value, it may be determined that the cleaning and sterilization of the tip has not been sufficiently performed.

From the determination in the scan target determination step S351 and the elapsed time determination step S353, when the scanned scan target is the inside of a patient's oral cavity and when the elapsed time is less than the elapsed time threshold value, it is determined that sufficient cleaning and sterilization have not been performed. Therefore, an operation restriction step S354 for restricting subsequent operations of the image processing apparatus may be performed. Accordingly, by restricting subsequent scanning with a tip that has not been sufficiently cleaned and sterilized, the patient may be provided with a hygienic treatment environment. However, the operation restriction step S354 may be deactivated by the user in some cases. Further, the operation restriction step S354 may be replaced by an operation that outputs a notification message instructing the user to clean and sterilize the tip, instead of completely restricting the scanning operation of the scanner.

At least some of the above-described steps may be visually displayed in a user interface on a display, and the user may easily view unique information and usage information of the tip.

Hereinafter, an image processing method according to a fourth embodiment of the present disclosure will be described.

Figure 18:
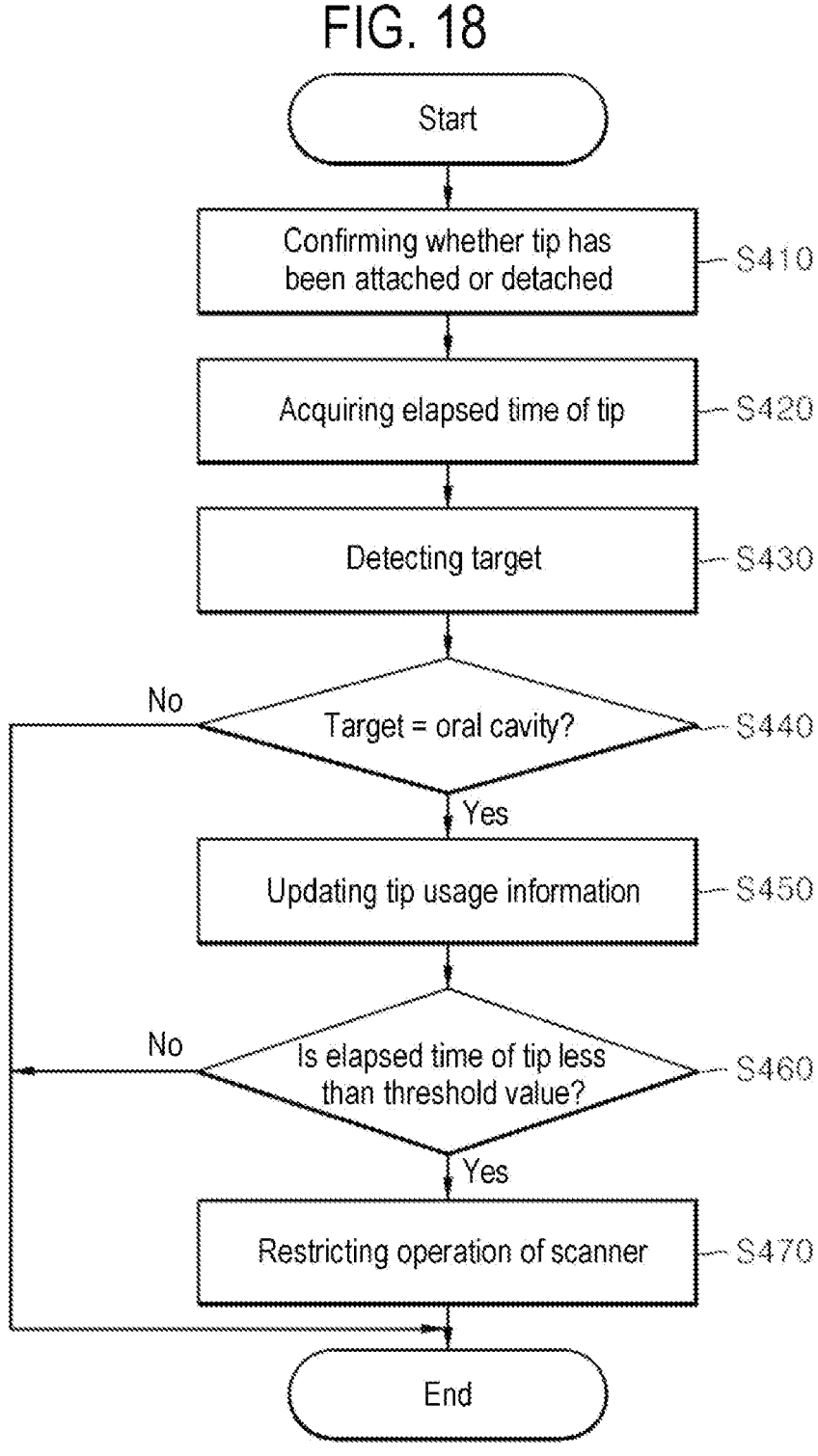
FIG. 18 is a flowchart of an image processing method according to a fourth embodiment of the present disclosure.

FIG. 18 is a flowchart of the image processing method according to the fourth embodiment of the present disclosure.

Referring to FIG. 18, the image processing method according to the fourth embodiment of the present disclosure may selectively update usage information of a tip according to the type of scan target even when the tip is not provided with an identifier, and may limit the operation of a scanner according to predetermined criteria.

The image processing method according to the fourth embodiment of the present disclosure includes an attachment/detachment confirmation step S410 of detecting whether the tip is attached to or detached from a scanner body. In the attachment/detachment confirmation step S410, whether the tip is attached to or detached from the scanner body may be detected through an attachment/detachment confirmation means formed on the scanner body. The attachment/detachment confirmation means may be at least one of a pressure sensor of a photosensor as described above, but is not limited thereto. The attachment/detachment confirmation step S410 is the same as the attachment/detachment confirmation step S310 of the third embodiment, and a detailed description thereof will be omitted.

Based on the determination in the attachment/detachment confirmation step S410, a usage information updating step S450 of updating the usage information of the tip may be performed when the tip is mounted on the scanner body. For example, updating the usage information of the tip may be updating (incrementing) the number of times the tip is used.

The usage information updating step S450 of updating the usage information of the tip may be selectively performed depending on the type of scan target, and the processes of detecting a target (S430) and determining the target (S440) based on the type of scan target are identical to the above-described steps having the same names.

Further, an elapsed time between detachment and reattachment of the tip from and to the scanner body may be acquired by the attachment/detachment confirmation means (S420). A step of controlling an operation of an image processing apparatus may be performed based on the acquired elapsed time. More specifically, whether the elapsed time is less than a threshold value may be determined in an elapsed time determination step S460, whether the scan target is the inside of a patient's oral cavity may be determined in the target determination step S440, and when the scan target is the inside of the patient's oral cavity and when the elapsed time is less than the threshold value, it is determined that sufficient cleaning and sterilization have not been performed, and an operation restriction step S470 of restricting an operation of the image processing apparatus may be performed.

The operational process of these steps is identical to that of the above-described steps having the same names.

Further, as described above, at least some of the aforementioned image processing methods may be displayed on a user interface through a display of the image processing apparatus, and a notification message may be output based on the usage information of the tip.

The above description is merely an exemplary description of the technical idea of the present disclosure, and a person skilled in the art, to which the present disclosure belongs, will appreciate that various modifications and variations are possible without departing from the essential features of the present disclosure.

Therefore, the embodiments disclosed in the present disclosure are intended to explain and not to limit the technical idea of the present disclosure, and the scope of the technical idea of the present disclosure is not limited by these embodiments. The scope of the present disclosure shall be construed on the basis of the accompanying claims in such a manner that all of the technical ideas included within the scope equivalent to the claims belong to the present disclosure.

INDUSTRIAL AVAILABILITY

The present disclosure provides an image processing apparatus and an image processing method using the same, wherein the image processing apparatus updates usage information of a tip via at least one of an attachment/detachment confirmation means and an identifier located inside the tip.

What is claimed is:

1. An image processing apparatus, comprising:
   a scanner body configured to scan a scan target to acquire data;
   a tip comprising an identifier, which has unique information, on one surface thereof and configured to be detachably coupled to the scanner body; and
   a controller configured to update usage information of the tip assigned to the unique information,
   wherein the tip comprises an optical member configured to change a path of light,
   wherein the scanner body comprises at least one camera configured to receive light of the scan target and the identifier,
   wherein image data generated from the light has an input area corresponding to an angle of view of the camera,
   wherein the input area comprises a first area, received in the camera through the optical member and formed as the image data, and a second area, received in the camera without going through the optical member and formed as the image data, and
   wherein the identifier is located in the second area.

2. The image processing apparatus of claim 1, wherein the tip comprises an optical member configured to change a path of light reflected from the scan target in order to receive the light in the scanner body, and
   wherein the identifier is disposed at one side of the optical member.

3. The image processing apparatus of claim 1, wherein the scanner body comprises at least one camera configured to receive light of the scan target and the identifier,
   wherein the identifier is formed of a material that is discolored in a predetermined environment, and
   wherein the controller is configured to provide a notification to a user in case that the camera does not detect the discolored identifier.

4. The image processing apparatus of claim 1, wherein the scanner body comprises at least one camera configured to receive light of the identifier, and
   wherein the camera is configured to detect the identifier before the tip is coupled to the scanner body.

5. The image processing apparatus of claim 1, wherein the controller comprises:
   an identifier detector configured to extract the unique information from the identifier;
   a data updater configured to selectively update the usage information of the tip assigned to the unique information; and
   a target detector configured to recognize a type of the scan target,
   wherein the controller is configured to selectively update the usage information of the tip according to the type of the scan target.

6. The image processing apparatus of claim 1, wherein at least one of the scanner body or the tip comprises a sensor configured to detect whether the tip has been attached or detached,
   wherein the controller comprises a checker configured to detect whether the tip has been attached to or detached from the scanner body, wherein the checker is configured to acquire, through the sensor, an elapsed time from detachment of the tip from the scanner body after scanning the scan target to reattachment of the tip thereto, and wherein, in case that the scan target is an oral cavity and the elapsed time is less than a threshold value, a scanning operation is restricted.

7. The image processing apparatus of claim 1, further comprising a display configured to display at least one of the unique information or the usage information on a user interface, wherein the display is configured to output, based on the usage information, a notification message on the user interface.

8. An image processing method comprising:

identifying unique information of a tip detachably coupled to a scanner body configured to scan a scan target; and updating usage information assigned to the identified unique information, wherein the tip comprises an optical member configured to change a path of light, wherein the scanner body comprises at least one camera configured to receive light of the scan target and the identifier, wherein image data generated from the light has an input area corresponding to an angle of view of the camera, wherein the input area comprises a first area, received in the camera through the optical member and formed as the image data, and a second area, received in the camera without going through the optical member and formed as the image data, and wherein the identifier is located in the second area.

9. The image processing method of claim 8, wherein an identifier, which has the unique information of the tip is located in an input area corresponding to an angle of view of at least one camera embedded in the scanner body, and wherein the identifying the unique information comprises:

detecting the identifier; and extracting the unique information of the tip from the identifier.

10. The image processing method of claim 8, wherein the identifier is disposed at one side of the optical member and is located in the second area.

11. The image processing method of claim 8, further comprising detecting the scan target, before the data updating the usage information, wherein in the updating the usage information, the usage information is selectively updated according to a type of the detected scan target.

12. The image processing method of claim 11, wherein in the updating the usage information, the usage information of the tip assigned to the unique information is updated in case that the scan target is an oral cavity.

13. The image processing method of claim 11, further comprising detecting attachment and detachment of the tip to and from the scanner body by a sensor formed on at least one of the scanner body or the tip, wherein in the detecting attachment and detachment of the tip, an elapsed time from detachment of the tip from the scanner body after scanning the scan target to reattachment of the tip thereto is acquired, and wherein, in case that the scan target is an oral cavity, the image processing method further comprises, after the detecting attachment and detachment of the tip, restricting a scanning operation when the elapsed time is less than a threshold value.

14. The image processing method of claim 8, wherein at least one of the unique information or the usage information of the tip is displayed on a user interface, and the user interface outputs a notification message based on the usage information.

* * * * *